(12) United States Patent
Chen et al.

(10) Patent No.: US 8,697,939 B2
(45) Date of Patent: Apr. 15, 2014

(54) MOUSE MODEL FOR DEPRESSION, SCHIZOPHRENIA AND ALZHEIMER'S DISEASE AND THE USE THEREOF

(75) Inventors: Yi-Ming Chen, Taipei (TW); Ching-Ping Yang, Taipei (TW)

(73) Assignee: National Yang Ming University, Taipei (TW)

( * ) Notice: Subject to any disclaimer, the term of this patent is extended or adjusted under 35 U.S.C. 154(b) by 112 days.

(21) Appl. No.: 13/161,817

(22) Filed: Jun. 16, 2011

(65) Prior Publication Data

US 2011/0283370 A1  Nov. 17, 2011

Related U.S. Application Data

(63) Continuation-in-part of application No. 12/431,641, filed on Apr. 28, 2009, now abandoned.

(51) Int. Cl.
*G01N 33/15* (2006.01)
*A01K 67/027* (2006.01)

(52) U.S. Cl.
USPC ................................................. 800/3; 800/18

(58) Field of Classification Search
USPC ....................................................... 800/3, 18
See application file for complete search history.

(56) References Cited

U.S. PATENT DOCUMENTS 7,759,542 B2 * 7/2010 Chen et al. ...................... 800/18
2009/0035290 A1 * 2/2009 Chen et al. ..................... 424/94.5

OTHER PUBLICATIONS

Clark et al. (2003) Nature Reviews: Genetics. vol. 4, 825-833.*
Niemann et al (2005) Rev. Sci, Tech. Off. Int. Spiz. vol. (24), 285-298.*
Wheeler (2001) Theriogenology. vol. 56, 1345-1369.*
Prelle et al. (2002) Anat. Histol. Embryol., vol. 31, 169-186.*
Doetschmann (1999) Lab. Animal Sci., vol. 49 (2), 137-143.*
Moens et al. (1993) Development, vol. 199, 485-499.*
Jacks et al. (1992) Nature, vol. 359, 295-300.*
Kuehn et al. (1987) Nature, vol. 326, 295-298.*
Jaenisch (1988) Science, vol. 240, 1468-1474.*
Powell et al. (2006, Biol. Psych., vol. 59, 1198-1207.*
Eui-Ju Yeo et al., "Tissue distribution of glycine N-methyltransferase, a major folate-binding protein of liver", Proc. Natl. Acad. Sc. USA, vol. 91, Jan. 1994, pp. 210-214.
Sylvia J. Kerr, "Competing Methyltransferase Systems, Journal of Biological Chemistry", vol. 247 No. 13, Issue of Jul. 10 pp. 4248-4252.
Hsiao-Han Liu et al., "Characterization of Reduced Expression of Glycine N-Methyltransferase in Cancerous Hepatic Tissues Using Two Newly Developed Monoclonal Antibodies", Journal of Biomedical Science, vol. 10, 2003, pp. 87-97.
Tzu-Ling Tseng et al., "Genotypic and Phenotypic Characterization of a Putative Tumor Susceptibility Gene", *GNMT*, in Liver Cancer, Cancer Research, vol. 63 Feb. 1, 2003, pp. 647-654.
Shih-Yin Chen et al., "Glycine N-Methyltransferase Tumor Susceptibility Gene in the Benzo(α)pyrene-Detoxification Pathway", Cancer Research, vol. 64 May 15, 2004, pp. 3617-3623.
P. Augoustides-Savvopoulou et al., "Glycine N-methyltransferase deficiency: a new patient with a novel mutation" J. Inherit. Metab. Dis. 26 (2003) pp. 745-759.
Moens et al., "Defects in heart and lung development in compound heterozygotes for two different targeted mutations at the N-*myc* locus" Development, vol. 199, pp. 485-499 (1993).
Jacks et al., "Effects of an *Rb* mutation in the mouse" Nature, vol. 359, pp. 295-300 (1992).
Kuehn et al., "A potential animal model for Lesch-Nyhan syndrome through introduction of HPRT mutations into mice" Nature, vol. 326, pp. 295-298 (1987).
Jaenisch "Transgenic Animals" Science, vol. 240, pp. 1468-1474 (1988).
Doetschman "Interpretation of Phenotype in Genetically Engineered Mice" Lab. Animal Sci., vol. 49 (2), pp. 137-143 (1999).
Campbell et al., "Totipotency or Multipotentiality of Cultured Cells: Applications and Progress" Theriogenology, vol. 47(1), pp. 63-72 (1997).
Li et al., "Germline Competent Embryonic Stem Cells Derived from Rat Blastocysts" Cell, vol. 135, pp. 1299-1310 (2008).
Powell et al., "Schizophrenia-Relevant Behavioral Testing in Rodent Models: A Uniquely Human Disorder?"Biol. Psych., vol. 59, pp. 1198-1207 (2006).

* cited by examiner

*Primary Examiner* — Anne Marie S Wehbe
(74) *Attorney, Agent, or Firm* — Muncy, Geissler, Olds & Lowe, P.C.

(57) ABSTRACT

The present invention relates to Glycine N-methyltransferase (GNMT) animal model and use thereof.

2 Claims, 11 Drawing Sheets
(1 of 11 Drawing Sheet(s) Filed in Color)

Figure 8
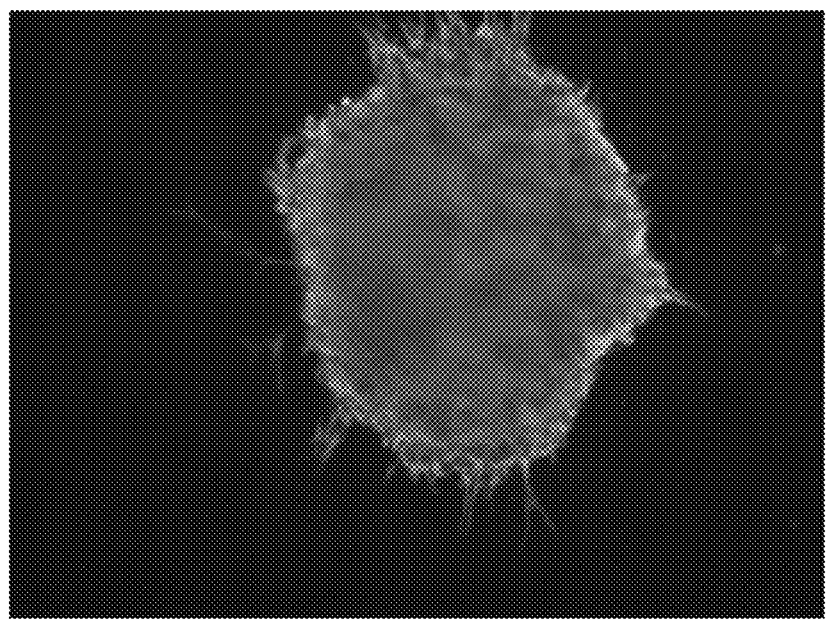
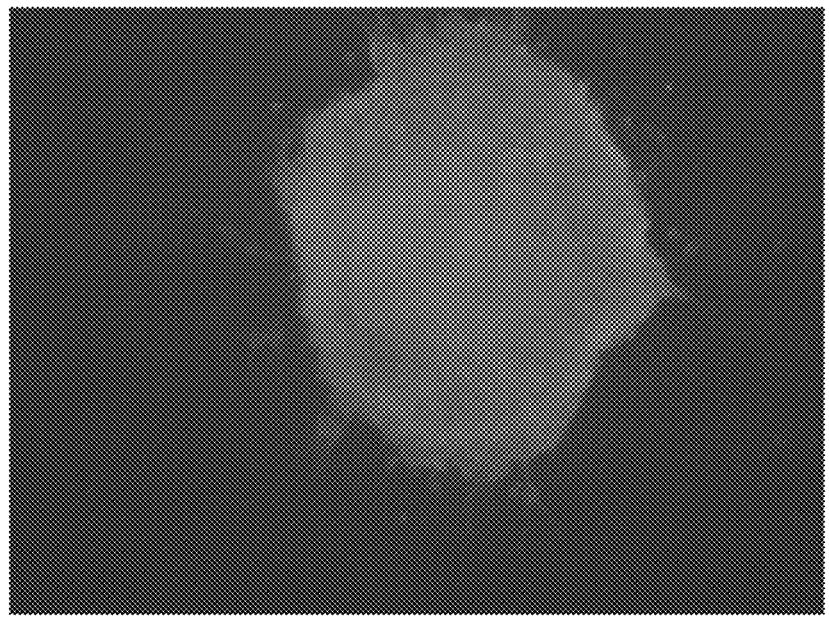

MOUSE MODEL FOR DEPRESSION, SCHIZOPHRENIA AND ALZHEIMER'S DISEASE AND THE USE THEREOF

CROSS-REFERENCE TO RELATED APPLICATION

This application is a continuation-in-part of application Ser. No. 12/431,641 filed Apr. 28, 2009.

FIELD OF THE INVENTION

The present invention relates to Glycine N-methyltransferase (GNMT) knockout animal model and use thereof.

BACKGROUND OF THE INVENTION

Glycine N-methyltransferase (GNMT), also known as a 4S polycyclic aromatic hydrocarbon (PAH) binding protein, has multiple functions. In addition to acting as a major folate binding protein (Yeo E J, et al. Proc Natl Acad Sci USA 1994; 91:210-214), it also regulates the ratio of S-adenosylmethionine (SAM) to S-adenosylhomocysteine (SAH) by catalyzing sarcosine synthesized from glycine (Kerr S J. J Biol Chem 1972; 247:4248-4252). It was previously reported that the GNMT gene is down-regulated in HCC (Liu H H, et al. J Biomed Sci 2003;10:87-97). Results from a genetic epidemiological study indicate that GNMT is a tumor susceptibility gene for liver cancer (Tseng T L, et al. Cancer Res 2003; 63:647-654). In addition, it was reported that GNMT binds benzo(a)pyrene and prevents DNA-adduct formation (Chen S Y, et al. Cancer Res 2004;64:3617-3623).

In mice, GNMT expression is regulated by growth hormone, with the hepatocytes of female mice having up to eight times the expression level normally found in male mice. There have been three reports of pediatric patients (two boys, one girl) with congenital GNMT deficiencies resulting from a missense mutation in the GNMT gene (Augoustides-Savvopoulou P, et al. J Inherit Metab Dis 2003; 26:745-759). All three children had hypermethioninaemia, clinical symptoms mimicking chronic hepatitis (Augoustides-Savvopoulou P, et al. J Inherit Metab Dis 2003; 26:745-759). The girl had stunted growth and suffered from mental deficiency (IQ 87).

The prior art disclosed a GNMT knock-out mouse which showed abnormal liver function and suffered from glycogen storage disease (U.S. application Ser. No. 11/832,304).

SUMMERY OF THE INVENTION

The present invention provides an animal model for studying depression, schizophrenia or Alzheimer's disease, wherein the animal model is a mammal whose genome is disrupted by recombination at Glycine N-methyltransferase (GNMT) gene locus.

The present invention also provides a method of generating an animal exhibiting a pathological condition of depression, schizophrenia or Alzheimer's disease, comprising disruption of GNMT gene in the animal by recombination at GNMT gene locus.

The present invention further provides a method for screening a drug candidate for treating depression, schizophrenia or Alzheimer's disease in a subject, comprising: (a) administering a potential drug candidate to the animal model of claim 1, (b) measuring the response of said animal to said drug candidate, (c) comparing the response of said animal with that of an animal having a wild type GNMT gene, and (d) selecting the drug candidate based on the difference in response observed between said animal and said animal having a wild type GNMT gene.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 8 shows that together with nestin (A), GNMT (B) expression was found on neural progenitor cell in immunofluoresencent images.

DETAILED DESCRIPTION OF THE INVENTION

Figure 1:
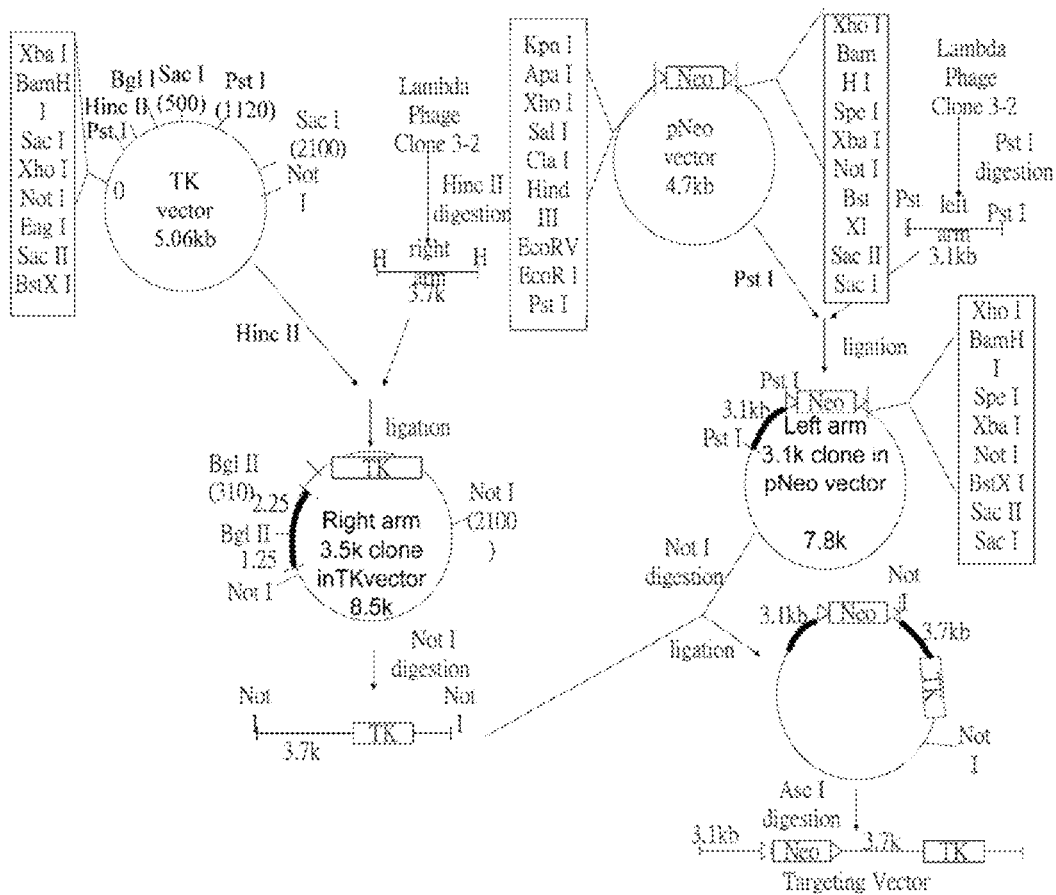
FIG. 1 shows the strategy of constructing the targeting vector.

The GNMT gene expresses in the neural progenitor cell and partial region of the brain, such as cerebral cortex, striatum, substantia nigra and cerebellum. Besides, the Depression-like and Schizo-like behaviors were observed in the Gnmt knock-out mouse model. Furthermore, the GNMT gene expresses in the mouse neuron cells which develops in vitro. Those results indicate the GNMT gene plays essential role in the function of brain and development.

According to the experimental results, it shows that metabolite of dopamine, dihydroxyphenylacetic acid, of the GNMT knock-out mouse is apparently reduced. Besides, it is observed that the GNMT knock-out mice display significant deficits in prepulse inhibition of the acoustic startle test compared with wild-type mouse. It is also observed that GNMT knock-out mouse is easier to give up to the TST (tail suspension test) and FST (forced swimming test). From the Rota-rod motor test, the result shows the exercise ability of GNMT knock-out mouse is inferior to that of wild-type mouse. The GNMT knock-out mouse presents Depression-like and Schizo-like behavior. Furthermore, the results of microarray show GNMT deficiency results in the increase expression of Alzheimer's disease related genes. Hence, the present animal model could be applied to research the Depression, Schizophrenia and Alzheimer's disease.

The animal model of this invention, wherein the animal includes but is not limited to mammal, primate, and rodent. In a preferable embodiment, the animal is mouse.

The present invention also provides a method of generating an animal exhibiting a pathological condition of depression, schizophrenia or Alzheimer's disease, comprising disruption of GNMT gene in the animal by recombination at GNMT gene locus. The pathological condition is characterized by deficits in prepulse inhibition of acoustic startle reflex, decreased immobility of tail suspension test and forced swim test, or elevating expression of Alzheimer's disease-associated genes. The elevating expression of Alzheimer's disease-associated genes includes but is not limited to BACE 1, BACE 2, APH-1, GSK-3, MAPT, and IDE.

The present invention further provides a method for screening a drug candidate for preventing or treating depression, schizophrenia or Alzheimer's disease in a subject, comprising: (a) administering a potential drug candidate to the animal model of the present invention, (b) measuring the response of said animal to said drug candidate, (c) comparing the response of said animal with that of an animal having a wild type GNMT gene, and (d) selecting the drug candidate based on the difference in response observed between said animal and said animal having a wild type GNMT gene.

As used herein, "drug candidate" means a composition of matter that is being investigated for a pharmacological or other activity or that is known to have a pharmacological or other activity, but is being tested to see if it has any type of activity in a particular subject, such as a patient. The drug candidate includes but is not limited to nucleic acid, peptide, and chemical compound. Efficacy of a drug candidate is one example of a pharmacological activity. Moreover, clinical outcome can be characterized as an activity of a drug candidate.

The present invention also provide a method for screening a drug candidate for treating depressing, schizophrenia or Alzheimer's disease in a subject, comprising: (a) providing a mammalian cell comprising a disruption in an endogenous GNMT gene, wherein the disruption results in a reduced level of an GNMT biological activity in the mammalian cell as compared to that of a wild type cell under identical conditions, (b) administering the potential drug candidate to the cell of step (a), and (c) comparing the response of said cell with that of a cell having a wild type GNMT gene, and (d) selecting the drug candidate based on the difference in response observed between said cell and said cell having a wild type GNMT gene. The method of the present invention, wherein the mammalian cell is present within a knockout non-human mammal, and the preferable cell is neural progenitor cell of brain.

EXAMPLES

Example 1

Preparing the GNMT Knock-out Mouse

To construct a targeting vector, DNA fragments digested from lambda phage clones 3-2 and 5-3 were inserted into a plasmid-pBluescrip II KS. Left arm was digested from the phage clone 5-3 by using Pst I and inserted into the pNeo vector. Right arm was digested from the phage clone 3-2 by using Hinc II and inserted into the TK vector. The fragment containing right arm and TK gene was digested by using Not I and inserted into the pNeo vector containing left arm to generate the targeting vector (FIG. 1).

Figure 2:
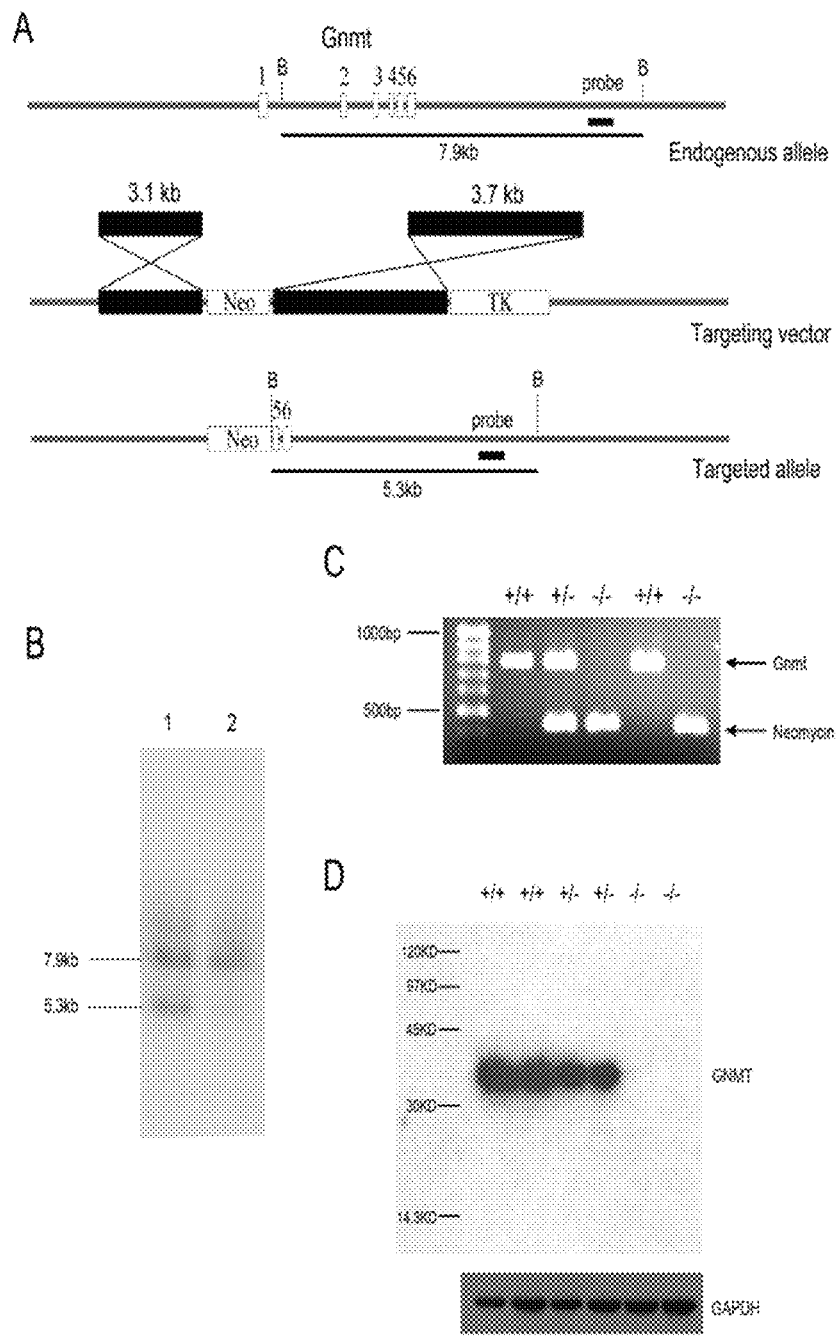
FIG. 2 shows targeted modification of the GNMT gene locus. (A) Targeting vector was designed to replace GNMT exons 1-4 and a part of exon 5 with a neomycin resistance gene. Neomycin positive selection marker is flanked by two homologous regions and followed by a TK negative selection marker at the 3' end of the targeting vector. (B) Southern blot analysis of embryonic stem cell clones. BamHI (B)-BamHI DNA fragment size decreased from 7.9 kb (wild-type allele) to 5.3 kb (recombinant allele). (C) Genotyping of GNMT knockout mice by PCR. The normal GNMT allele yielded a 772 bp fragment and the disrupted allele a 409 bp fragment. +/+, wild-type; +/−, GNMT heterozygous and −/−, GNMT−/− mice (D) Expression of GNMT protein confirmed by western blot analysis. Each lane contains 10 µg hepatic lysate. GNMT molecular mass: 32 kDa. GAPDH: internal control.

The neomycin gene (to replace exons 1-4 and part of exon 5 of the mouse Gnmt gene) was framed with two DNA fragments (3.1 kb and 3.7 kb) in the targeting vector. The thymidine kinase gene was used as a negative selection marker (FIG. 2A). The 40 μg targeting vector was linearized using AscI and introduced into embryonic stem cells (129/Sv-derived) by electroporation. After screening 278 clones using southern blot analysis (FIG. 2B), a recombinant clone was isolated and used for microinjection into blastocytes. Four male chimeric mice were obtained and used to breed female C57BL/6 mice. Agouti $F_1$ offspring were subjected to PCR to detect the germline transmission of the disrupted allele. Heterozygous $F_1$ male mice were backcross with female wild-type C57B/6 mice to generate C57BL/6 genome background mice.

PCR was developed to differentiate wild-type (+/+), GNMT heterozygous (+/−), and GNMT−/− mice. The primers used for PCR were shown as the following: GNMT-F (5'-GCGGCGGCCGCATGCTGGTGGAAGAGGGC, SEQ ID NO. 1) and GNMT-R (5'-TTGCAGTCTGGCAAGT-GAGC, SEQ ID NO. 2) for GNMT; neomycin-F (5'-GTTC-CTTGCGCAGCTGTGCT, SEQ ID NO. 3) and neomycin-R (5'-CGGCCACAGTCGATGAATCC, SEQ ID NO. 4) for neomycin. The normal GNMT allele yielded a 772 bp fragment by GNMT primers and the disrupted allele yielded a 409 bp fragment by neomycin primers (FIG. 2C). The expression of GNMT protein in liver was analyzed using western blot; the results show that compared to the wild-type, GNMT expression decreased approximately 50% in the livers of GNMT+/− mice and GNMT was undetectable in the livers of GNMT−/− mice (FIG. 2D).

Example 2

Prepulse Inhibition (PPI) of Startle Reflex

The apparatus consisted of two startle chambers (Med Associates, Georgia, Vt.). One mouse selected from the WT control group and the other selected from GNMT deficient group were tested simultaneously. Each mouse was put into the PPI chamber for a 5-min acclimatization period with a 60 dB background noise. Following this period, 10 startle pulses (120 dB, 40 ms duration) were presented with an average inter-trial interval of 15 s. Then, no stimulus (background noise, 68 dB), prepulses alone (72, 76 and 84 dB, 20 ms duration), startle pulses alone, and prepulses followed 80 ms later by startle pulses were presented six times randomly distributed over the next 20 min.

Figure 3:
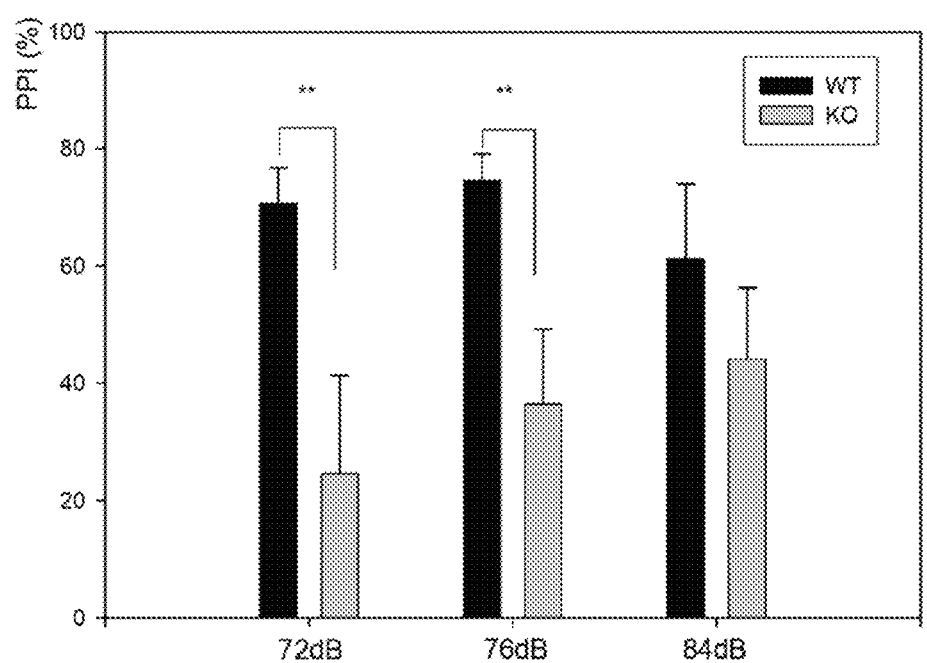
FIG. 3 shows GNMT−/− male mice displayed significant deficits in prepulse inhibition of the acoustic startle reflex. Data are presented as mean± S.E.M.; ** p <0.01.

PPI was defined as the percentage reduction of startle magnitude in the presence of the prepulse compared to the magnitude in the absence of the prepulse. % PPI=[1-(prepulse trials/startle-only trials)] ×100. FIG. 3 showed GNMT$^{-/-}$ mice displayed significant deficits in prepulse inhibition of the acoustic startle reflex.

Example 3

Figure 4:
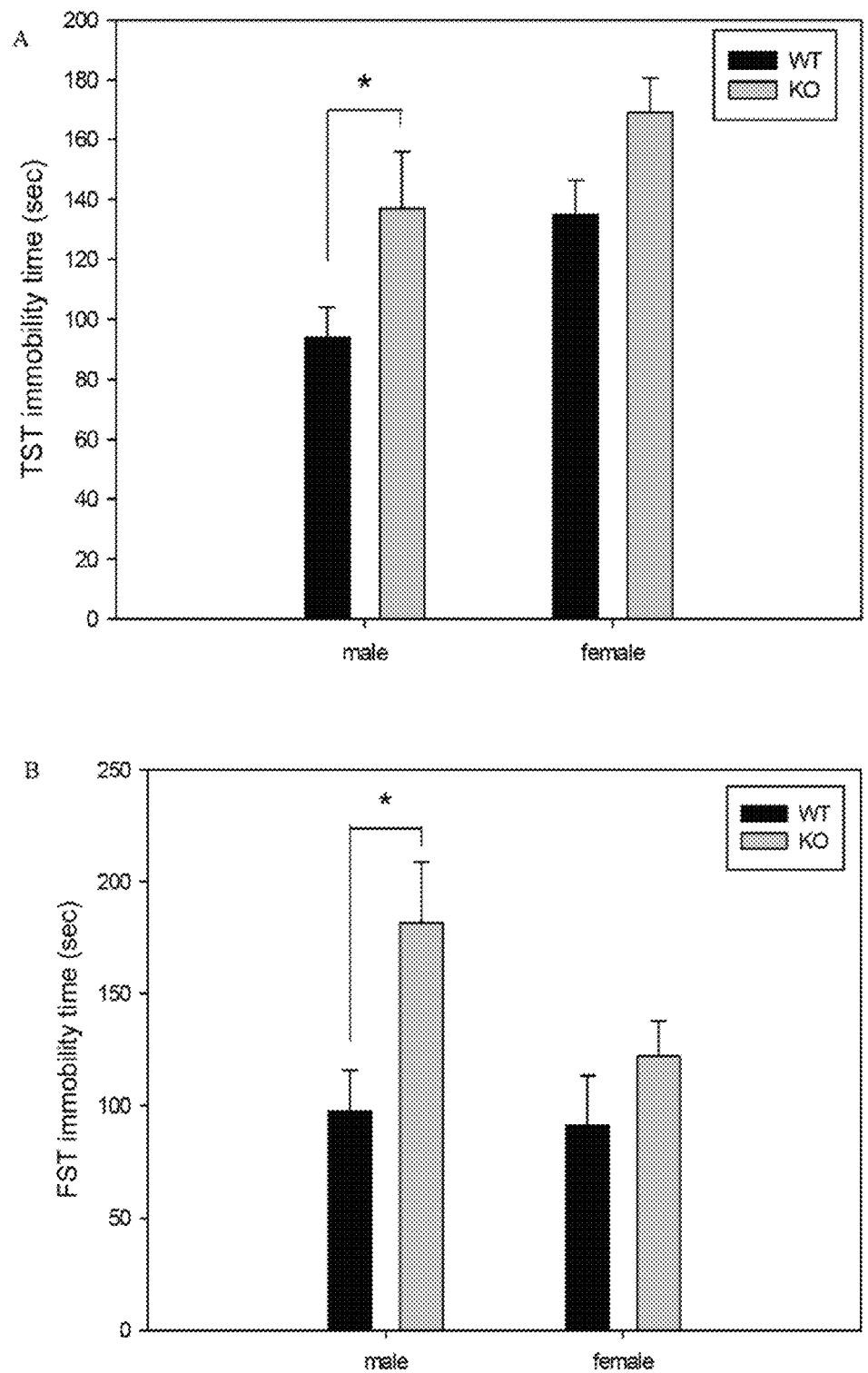
FIG. 4 shows using TST and FST, GNMT−/− displayed significant increased immobility in the TST (A) and FST (B). Data are presented as mean± S.E.M.; * p<0.05.

Tail Suspension Test 8-12 weeks old male and female mice were suspended by the tail. After 'agitation' or 'escape-like' behavior, mice adopted an immobile posture, suggested to mirror a state of depression. The immobility time during a 5 min test recorded. The result of FIG. 4A showed that GNMT$^{-/-}$ mice displayed significant decreased immobility.

Example 4

Forced Swim Test 8-12 weeks old male and female mice were placed (n=11 per WT and n=13 per KO) individually in rectangular cage (height 30 cm, diameter 15 cm) filled with 12-cm-deep water (temperature 22 ±1° C.) for 6 min. The processes of the total period of immobility during the last 5 min were recorded. The immobility of GNMT$^{-/-}$ mice was decrease in the FIG. 4B. Immobility was defined as the absence of initiated movements and includes passive swaying.

Example 5

Analysis of Motor Activity

Figure 5:
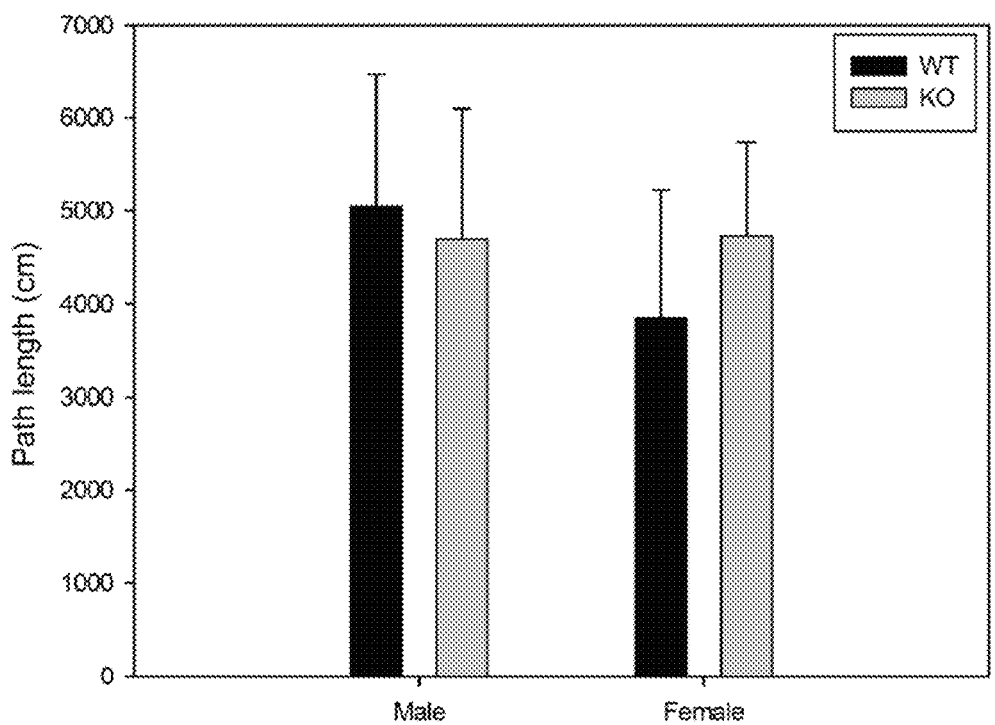
FIG. 5 shows that no significant difference of locomotor activity was found between both genders of WT and GNMT−/− mice.

GNMT$^{-/-}$ animal and their wild-type were individually tested for motor activity at 8-12 weeks of age under 90 cm×90 cm×30 cm open field. Each mouse was tested for 10 min between 1700 and 1900 h. The results shown in FIG. 5 were generated online by the TrackMot software package. There was no significant difference found between both sexes of WT and GNMT$^{-/-}$ mice.

Example 6

Rotarod Testing

Figure 6:
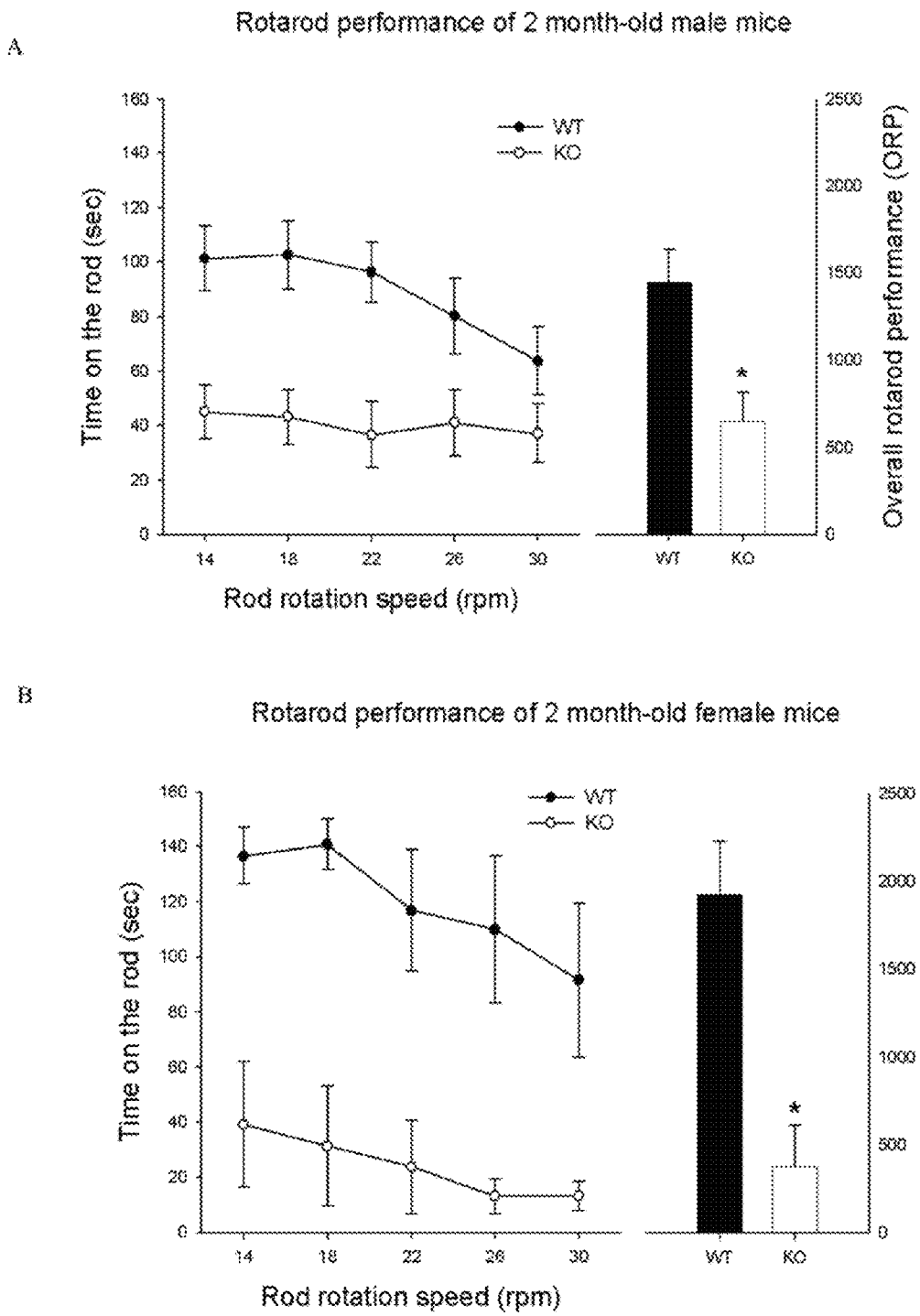
FIG. 6 shows GNMT−/− mice having motor deficits of shorter latency of falling from the Rotating rod task. Data are presented as mean±S.E.M.; * p<0.05.

On the day of testing, all animals were transferred to the test room at least half an hour earlier. Then the mice were tested on a rotarod apparatus which consisted of a rotating rod (diameter, 3 cm; hard non-slipping plastic). All mice were habituated to the apparatus for at least four consecutive trials in which the rod was kept at constant speed (one trial at 0 rpm and three trials at 5 rpm) with 5 minutes interval. Once the trained animals were able to stay on the rod rotating at 5 rpm for 60 seconds in three consecutive trials, they proceeded to the test. Three trials at each of five fixed rotating speeds (14, 18, 22, 26, and 30 rpm) were sequentially conducted for a maximum of 150 seconds each speed or until the animals fell off. The length of time that each animal was able to stay on the rod at each rotation speed was recorded (latency to fall). Regardless of completion or fall, each animal was allowed to rest for at least 5 minutes between individual testing speeds and 30 minutes between each complete trial. The mean of overall rod performance (ORP) for the three trials of each mouse was calculated by the trapezoidal method as the area under the curve in the plot of latent time on the rod versus rotation speed. (FIG. 6)

Example 7

RNA Isolation and RT-PCR

Total RNA was extracted from tissues using TRIzol (Invitrogen, Carlsbad, Calif.). Complementary DNA was produced from olfactory bulb, cortex, striatum, midbrain, cerebellum, spinal cord, hippocampus, hypothalamus, medulla and brain stem RNA (5 µg) using a SuperScript II Reverse Transcriptase Kit (Invitrogen). PCR conditions were pre-denaturated at 94° C. for 5 minutes followed by 30 cycles of amplification at 94° C. for 30 seconds, 60° C. for 30 seconds, and 72° C. for 1 min, followed by a 10-minute extension step at 72° C. The primer sequences are followings: m-GNMT-F (5'-GCGGCGGCCG-CATGCTGGTGGAAGAGGGC, SEQ ID NO. 5) and m-GNMT-R (5'-TTGCAGTCTGGCAAGTGAGC, SEQ ID NO. 6) for GNMT; β-actin-F (5'-GGGCGCCCCAG-GCACCA, SEQ ID NO. 7) and β-actin-R (5'-CTCCTTAAT-GTCACGCCGATTTC, SEQ ID NO. 8) for β-actin.

Example 8

Real-Time PCR

Ten genes belonging to the Alzheimer Disease pathway were selected for real-time PCR analysis. Real-time PCR primers were designed using PRIMER EXPRESS software (Version 2.0, Applied Biosystems) and verified the specificity of sequences using BLAST. Reactions were performed in 10 µl quantities of diluted cDNA sample, primers (100 nM), and a SYBR Green PCR Master Mix containing nucleotides. Reactions were assayed using an Applied Biosystems Prism 7000 sequence detection system.

After cycling, a melting curve was produced via the slow denaturation of PCR end products to validate amplification specificity. Predicted cycle threshold ($C_T$) values were exported into EXCEL worksheets for analysis. Comparative $C_T$ methods were used to determine relative gene expression folds to GAPDH. The primers used for real-time PCR were shown as the followings: APP-F (5'-GCCAGCCAATAC-CGAAAATG, SEQ ID NO. 9) and APP-R (5'-GATGTTTGT-CAGCCCAGAACCT, SEQ ID NO. 10) for APP; BACE1-F (5'-ACGACTCTTTGGAGCCCTTCT, SEQ ID NO. 11) and BACE1-R (5'-AGAGCTGCAGGGAAAAGATGTT, SEQ ID NO. 12) for BACE1 for BACE; BACE2-F (5'-CACG-GAAGACATAGCCAGCAA, SEQ ID NO. 13) and BACE2-R (5'-TCAGGGCATAGGACACAATCC, SEQ ID NO. 14) for BACE2; IDE-F (5'-CGTCCAATCTGATGGC-GATT, SEQ ID NO. 15) and IDE-R (5'-AGAACAGCT-TCACCACCAGGTTA, SEQ ID NO. 16) for IDE; SNCA-F (5'-AAACACCTAAGTGACTACCACTTATTTCTAAA, SEQ ID NO. 17) and SNCA-R (5'-TCTTGGAGCAAATCA-CAACTTCTT, SEQ ID NO. 18) for SNCA; MAPT-F (5'-AGCAATGAGAGATTTGAGACTTGGT, SEQ ID NO. 19) and MAPT-R (5'-CCTTCGCTGTCGCTGTTTC, SEQ ID NO. 20) for MAPT; APH1α-F (5'-ATGCACGGCTCCAG-TATGG, SEQ ID NO. 21) and APH1α-R (5'-GCAAAACG-GAACACTTCCTGTAG, SEQ ID NO. 22) for APH1α; GSK3β-F (5'-CGGGACCCAAATGTCAAACT, SEQ ID NO. 23) and GSK3β-R (5'-TCCGAGCATGTGGAGG-GATA, SEQ ID NO. 24) for GSK3β; GAPDH-F (5'-TGG- TATCGTGGAAGGACTCA, SEQ ID NO. 25) and GAPDH-R (5'-AGTGGGTGTCGCTGTTGAAG, SEQ ID NO. 26) for GAPDH.

Figure 7:
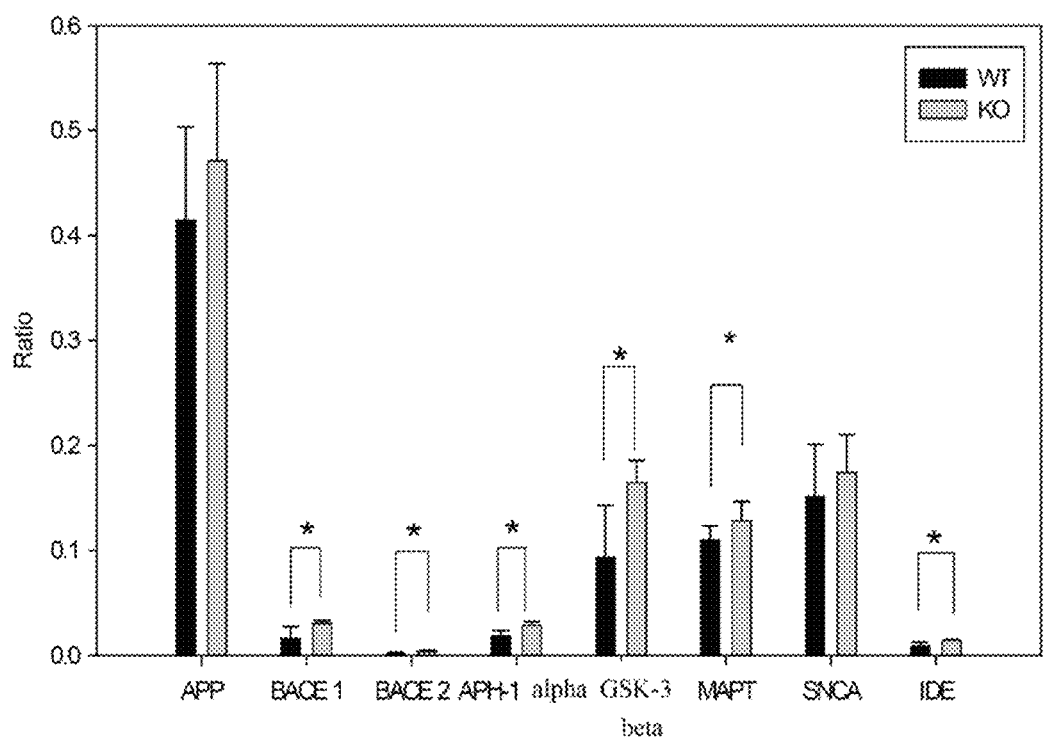
FIG. 7 shows comparing the following Alzheimer's Disease associated mRNA expression in the cerebral cortex of one-month old mice by Q-PCR, as follows, APP, BACE 1, BACE 2, APH-1α, GSK-3β, MAPT, SNC60 and IDE. Data are presented as mean± S.E.M.; * p<0.05.

As showed in FIG. 7, the expression level of genes coding for β-amyloid precursor protein cleaving enzyme, such as BACE1 and BACE2, and for Tau protein phosphorylation regulatory protein, such as GSK-3b and MAPT, were significantly elevated in GNMT knockout mice. The phosphorylation of Tau protein on neural cell is a typical symptom of Alzheimer's disease (Barten D M, Albright C F. (2008) Therapeutic strategies for Alzheimer's disease. *Mol Neurobiol.* 37(2-3): 171-86). Although the expression level of β-amyloid precursor (APP) protein was not significantly changed in GNMT knockout mice, the expression level of APP cleaving enzymes, BACE1 and BACE2, were significantly higher than expressed in wild-type mice. According to the results of Microarray and Real-Time PCR, Applicant reasonably concluded that GNMT deficiency may induce the deposition of β-amyloid in brain, and further causes symptoms of Alzheimer's disease, such as memory degeneration.

Example 9

Immunofluorescent Staining

Neural progenitor cell culture followed the protocol by Zhou. et al. After 7 or 10 days in the culture of subplating, the subcultures were washed with cold 0.1 M PBS three times and then fixed with 4% paraformaldehyde for 4 h and permeated with 0.1% Triton X-100 for 30 min. The phenotypic expression of the neurospheres was examined using immunocytochemical staining with antibodies against (a) Nestin (1:500) (BD Biosciences) for neuroepithelial stem cells or (b) GNMT (1:250). (FIG. 8)

Example 10

Immunohistochemistry

Figure 9:
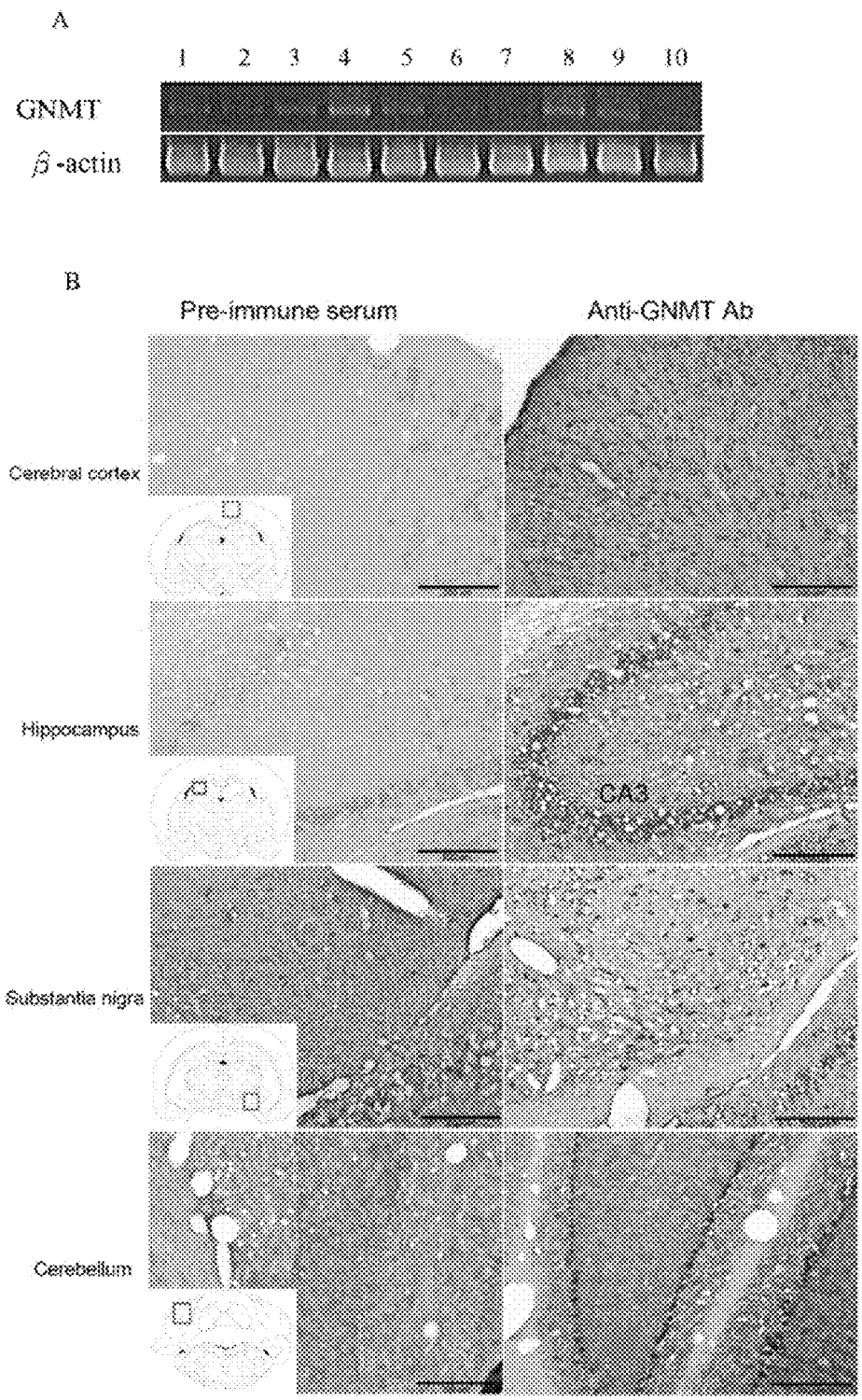
FIG. 9 shows detecting of GNMT expression in WT mouse brain (A) GNMT mRNA in different parts of mouse brain using RT-PCR. 1) olfactory bulb, 2) cortex, 3) striatum, 4) midbrain, 5) cerebellum, 6) spinal cord, 7) hippocampus, 8) thalamus and hypothalamus, 9) pons and medulla, 10) brain stem. (B) Immunostaining of GNMT in WT mice brain.

Isolated brain tissues of WT mice are fixed in 10% neutral-buffered formalin. After infiltrating with 30% sucrose solution in PBS, cut the tissue using frozen sections and paraffin sections (method). For antigen retrieval, tissue sections on slides were immersed in borate buffer solution (pH 8) jar and placed in pressure oven for about 20 min until the cooker reached its maximum pressure. It was then heated for another 5 min at maximum pressure. Thereafter, the pressure was reduced and cooled in a bath of tap water. Then the sections incubate in blocking solution at room temperature for 6 hours. And they were incubated overnight at 4° C. with the following rabbit anti-GNMT sera at 1/100. After washing in PBS, these slides were incubated with biotinylated antibody and peroxidase-labeled streptavidin (DAKO, Carpinteria, Calif.) for 10 min at room temperature. These slides were further incubated with 3,3'-diaminobenzidine tetrahydrochloride solution for color reaction. (FIG. 9)

Example 11

Statistical Analysis

All data were pooled according to genotype, and a mean value was determined for each group. Results were presented as means ± SEM and were analyzed by ANOVA and Student's t-test with $p \leq 0.05$ used as significance criteria.

Example 12

Figure 10:
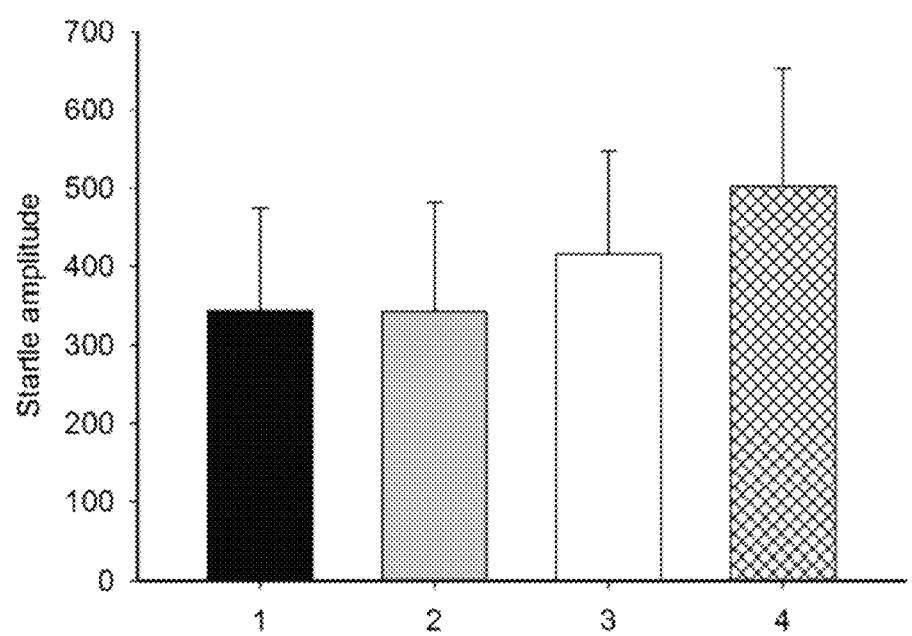
FIG. 10 shows the effect of clozapine and sarcosine treatment on the startle amplitude in Gnmt−/− mice. Bar 1, wild-type treated with PBS; Bar 2, Gnmt−/− treated with PBS; Bar 3, Gnmt−/− treated with clozapine; Bar 4, Gnmt−/− treated with sarcosine.
Figure 11:
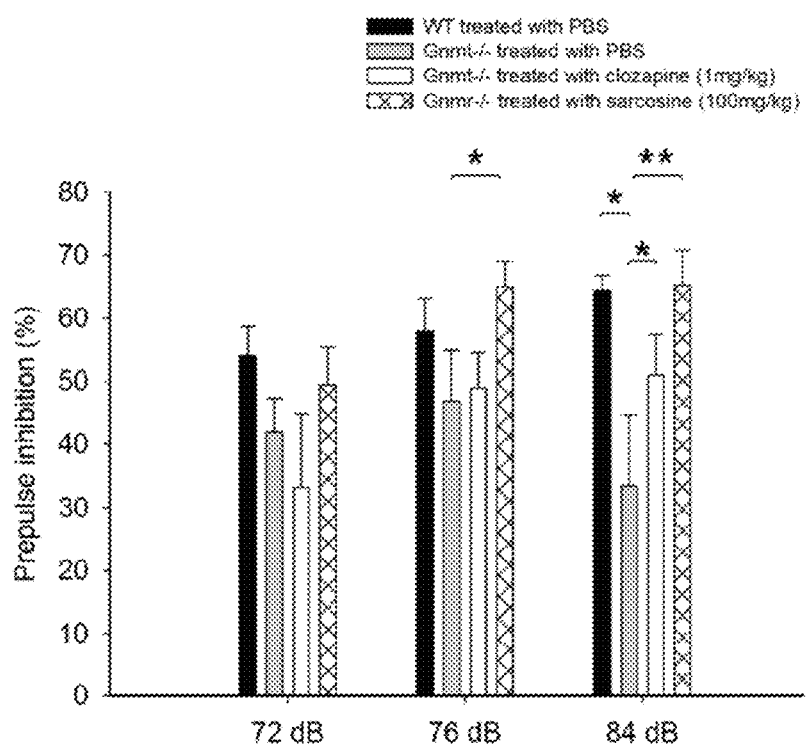
FIG. 11 shows the effect of clozapine and sarcosine on percent PPI of ASR. Gnmt−/− mice treated with clozapine or sarcosine displayed significantly induced PPI when compared with their solvent control. Data are presented as means ± SEM; *p<0.05, **p<0.01.

Use of $GNMT^{-/-}$ Mice for Screening a Drug Candidate for Treating Depression, Schizophrenia or Alzheimer's Disease in a Subject In view of the observed deficits in prepulse inhibition (PPI) of the acoustic startle reflex in GNMT knockout mice, we administered clozapine (a classical anti-schizophrenic drug, 1 mg/kg) to the GNMT knockout mice, and evaluated the therapeutic effects on schizophrenia. As showed in FIG. 10, the administration of clozapine did not significantly affect the level of startle amplitude. In contrary, Gnmt-/- mice treated with clozapine displayed significantly induced PPI when compared with their solvent control. (FIG. 11).

Another hypothesis of schizophrenia pathology is that neuropsychiatric disorder may be associated with the dysfunction of N-methyl-D-aspartate (NMDA) receptor, a glutamate receptor. The development of new drugs for treating schizophrenia is increasingly focused on enhancing the function of NMDA receptor. Nowadays, to enhance the natural amino acid NMDA receptor glycine is of most possibility, and there are some tentative clinical studies showing positive effects. For example, in clinical studies, the supplement of sarcosine to inhibit glycine transporter-1 can improve the symptoms of schizophrenia. Additionally, it is reported that the administration of sarcosine in phase II clinical trials is effective to ameliorate symptoms of depression. Therefore, in a further experiment, sarcosine (100 mg/kg) is administered to the GNMT knockout mice, and evaluated its therapeutic effects on schizophrenia. As showed in FIG. 11, The GNMT-/- mice treated with sarcosine displayed significantly ameliorated deficits in prepulse inhibition of the acoustic startle reflex, and the level of startle amplitude is unaffected as observed in clozapine treated mice (FIG. 10).

In conclusion, the GNMT knockout mouse is a useful animal model for studying depression, schizophrenia or Alzheimer's disease, especially for schizophrenia in this example. Furthermore, it is possible to use this animal model in screening and/or developing a drug candidate for treating schizophrenia by blocking glycine transporter-1 in a subject.

One skilled in the art readily appreciates that the present invention is well adapted to carry out the objects and obtain the ends and advantages mentioned, as well as those inherent therein. The cell lines, animals, and processes and methods for producing them are representative of preferred embodiments, are exemplary, and are not intended as limitations on the scope of the invention. Modifications therein and other uses will occur to those skilled in the art. These modifications are encompassed within the spirit of the invention and are defined by the scope of the claims.

It will be readily apparent to a person skilled in the art that varying substitutions and modifications may be made to the invention disclosed herein without departing from the scope and spirit of the invention.

All patents and publications mentioned in the specification are indicative of the levels of those of ordinary skill in the art to which the invention pertains. All patents and publications are herein incorporated by reference to the same extent as if each individual publication was specifically and individually indicated to be incorporated by reference.

The invention illustratively described herein suitably may be practiced in the absence of any element or elements, limitation or limitations, which are not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention claimed. Thus, it should be understood that although the present invention has been specifically disclosed by preferred embodiments and optional features, modification and variation of the concepts herein disclosed may be resorted to by those skilled in the art, and that such modifications and variations are considered to be within the scope of this invention as defined by the appended claims.

What is claimed is:

1. A method for screening a candidate drug for treating depression like behavior in a subject, comprising:
   (a) administering a potential candidate drug to a male GNMT$^{-/-}$ mouse model whose genome is homozygously disrupted by recombination at Glycine N-methyltransferase (GNMT) gene locus, wherein the mouse model exhibits a depression-like behavior in increased immobility times in tail suspension test (TST) and forced swim test (FST) as evaluated in a behavioral test,
   (b) measuring the response in the pathological condition of the GNMT knockout mouse to said drug candidate,
   (c) comparing the depression-like behavior in TST and FST measured in step (b) with that of a male mouse having a wild type GNMT gene, and
   (d) selecting the drug candidate based on the improved depression-like behavior in TST and FST in the response measured after the administration of said drug candidate and the comparison with the wild type mouse.

2. A method for screening a candidate drug for treating schizophrenia-like behavior in a subject, comprising:
   (a) administering a potential candidate drug to a GNMT$^{-/-}$ mouse model whose genome is homozygously disrupted by recombination at Glycine N-methyltransferase (GNMT) gene locus, wherein the mouse model exhibits a schizophrenia-like behavior in prepulse inhibition of acoustic startle reflex (PPI) as evaluated in a behavioral test,
   (b) measuring the response in the schizophrenia-like behavior in PPI of the GNMT knockout mouse to said drug candidate,
   (c) comparing the schizophrenia-like behavior in PPI measured in step (b) with that of a mouse having a wild type GNMT gene, and
   (d) selecting the drug candidate based on the improved schizophrenia-like behavior in PPI in the response measured after the administration of said drug candidate and the comparison with the wild type mouse.

* * * * *

SEQUENCE LISTING

```
<160> NUMBER OF SEQ ID NOS: 26

<210> SEQ ID NO 1
<211> LENGTH: 29
<212> TYPE: DNA
<213> ORGANISM: Artificial Sequence
<220> FEATURE:
<223> OTHER INFORMATION: GNMT-F
<220> FEATURE:
<221> NAME/KEY: misc_feature
<222> LOCATION: (1)..(29)

<400> SEQUENCE: 1
gcggcggccg catgctggtg gaagagggc                              29

<210> SEQ ID NO 2
<211> LENGTH: 20
<212> TYPE: DNA
<213> ORGANISM: Artificial Sequence
<220> FEATURE:
<223> OTHER INFORMATION: GNMT-R
<220> FEATURE:
<221> NAME/KEY: misc_feature
<222> LOCATION: (1)..(20)

<400> SEQUENCE: 2
ttgcagtctg gcaagtgagc                                        20

<210> SEQ ID NO 3
<211> LENGTH: 20
<212> TYPE: DNA
<213> ORGANISM: Artificial Sequence
<220> FEATURE:
<223> OTHER INFORMATION: neomycin-F
<220> FEATURE:
<221> NAME/KEY: misc_feature
<222> LOCATION: (1)..(20)

<400> SEQUENCE: 3
gttccttgcg cagctgtgct                                        20

<210> SEQ ID NO 4
<211> LENGTH: 20
<212> TYPE: DNA
<213> ORGANISM: Artificial Sequence
<220> FEATURE:
<223> OTHER INFORMATION: neomycin-R
<220> FEATURE:
<221> NAME/KEY: misc_feature
<222> LOCATION: (1)..(20)

<400> SEQUENCE: 4
cggccacagt cgatgaatcc                                        20

<210> SEQ ID NO 5
<211> LENGTH: 29
<212> TYPE: DNA
<213> ORGANISM: Artificial Sequence
<220> FEATURE:
<223> OTHER INFORMATION: m-GNMT-F
<220> FEATURE:
<221> NAME/KEY: misc_feature
<222> LOCATION: (1)..(29)

<400> SEQUENCE: 5
gcggcggccg catgctggtg gaagagggc                              29
```

```
<210> SEQ ID NO 6
<211> LENGTH: 20
<212> TYPE: DNA
<213> ORGANISM: Artificial Sequence
<220> FEATURE:
<223> OTHER INFORMATION: m-GNMT-R
<220> FEATURE:
<221> NAME/KEY: misc_feature
<222> LOCATION: (1)..(20)

<400> SEQUENCE: 6
ttgcagtctg gcaagtgagc                                              20

<210> SEQ ID NO 7
<211> LENGTH: 17
<212> TYPE: DNA
<213> ORGANISM: Artificial Sequence
<220> FEATURE:
<223> OTHER INFORMATION: beta-actin-F
<220> FEATURE:
<221> NAME/KEY: misc_feature
<222> LOCATION: (1)..(17)

<400> SEQUENCE: 7
gggcgcccca ggcacca                                                 17

<210> SEQ ID NO 8
<211> LENGTH: 23
<212> TYPE: DNA
<213> ORGANISM: Artificial Sequence
<220> FEATURE:
<223> OTHER INFORMATION: beta-actin-R
<220> FEATURE:
<221> NAME/KEY: misc_feature
<222> LOCATION: (1)..(23)

<400> SEQUENCE: 8
ctccttaatg tcacgccgat ttc                                          23

<210> SEQ ID NO 9
<211> LENGTH: 20
<212> TYPE: DNA
<213> ORGANISM: Artificial Sequence
<220> FEATURE:
<223> OTHER INFORMATION: APP-F
<220> FEATURE:
<221> NAME/KEY: misc_feature
<222> LOCATION: (1)..(20)

<400> SEQUENCE: 9
gccagccaat accgaaaatg                                              20

<210> SEQ ID NO 10
<211> LENGTH: 22
<212> TYPE: DNA
<213> ORGANISM: Artificial Sequence
<220> FEATURE:
<223> OTHER INFORMATION: APP-R
<220> FEATURE:
<221> NAME/KEY: misc_feature
<222> LOCATION: (1)..(22)

<400> SEQUENCE: 10
gatgtttgtc agcccagaac ct                                           22

<210> SEQ ID NO 11
<211> LENGTH: 21
<212> TYPE: DNA
<213> ORGANISM: Artificial Sequence
<220> FEATURE:
```

```
<223> OTHER INFORMATION: BACE1-F
<220> FEATURE:
<221> NAME/KEY: misc_feature
<222> LOCATION: (1)..(21)

<400> SEQUENCE: 11
acgactcttt ggagcccttc t                                              21

<210> SEQ ID NO 12
<211> LENGTH: 22
<212> TYPE: DNA
<213> ORGANISM: Artificial Sequence
<220> FEATURE:
<223> OTHER INFORMATION: BACE1-R
<220> FEATURE:
<221> NAME/KEY: misc_feature
<222> LOCATION: (1)..(22)

<400> SEQUENCE: 12
agagctgcag ggaaaagatg tt                                             22

<210> SEQ ID NO 13
<211> LENGTH: 21
<212> TYPE: DNA
<213> ORGANISM: Artificial Sequence
<220> FEATURE:
<223> OTHER INFORMATION: BACE2-F
<220> FEATURE:
<221> NAME/KEY: misc_feature
<222> LOCATION: (1)..(21)

<400> SEQUENCE: 13
cacggaagac atagccagca a                                              21

<210> SEQ ID NO 14
<211> LENGTH: 21
<212> TYPE: DNA
<213> ORGANISM: Artificial Sequence
<220> FEATURE:
<223> OTHER INFORMATION: BACE2-R
<220> FEATURE:
<221> NAME/KEY: misc_feature
<222> LOCATION: (1)..(21)

<400> SEQUENCE: 14
tcagggcata ggacacaatc c                                              21

<210> SEQ ID NO 15
<211> LENGTH: 20
<212> TYPE: DNA
<213> ORGANISM: Artificial Sequence
<220> FEATURE:
<223> OTHER INFORMATION: IDE-F
<220> FEATURE:
<221> NAME/KEY: misc_feature
<222> LOCATION: (1)..(20)

<400> SEQUENCE: 15
cgtccaatct gatggcgatt                                                20

<210> SEQ ID NO 16
<211> LENGTH: 23
<212> TYPE: DNA
<213> ORGANISM: Artificial Sequence
<220> FEATURE:
<223> OTHER INFORMATION: IDE-R
<220> FEATURE:
<221> NAME/KEY: misc_feature
<222> LOCATION: (1)..(23)
```

```
<400> SEQUENCE: 16
agaacagctt caccaccagg tta                                          23

<210> SEQ ID NO 17
<211> LENGTH: 32
<212> TYPE: DNA
<213> ORGANISM: Artificial Sequence
<220> FEATURE:
<223> OTHER INFORMATION: SNCA-F
<220> FEATURE:
<221> NAME/KEY: misc_feature
<222> LOCATION: (1)..(32)

<400> SEQUENCE: 17
aaacacctaa gtgactacca cttatttcta aa                                32

<210> SEQ ID NO 18
<211> LENGTH: 24
<212> TYPE: DNA
<213> ORGANISM: Artificial Sequence
<220> FEATURE:
<223> OTHER INFORMATION: SNCA-R
<220> FEATURE:
<221> NAME/KEY: misc_feature
<222> LOCATION: (1)..(24)

<400> SEQUENCE: 18
tcttggagca aatcacaact tctt                                         24

<210> SEQ ID NO 19
<211> LENGTH: 25
<212> TYPE: DNA
<213> ORGANISM: Artificial Sequence
<220> FEATURE:
<223> OTHER INFORMATION: MAPT-F
<220> FEATURE:
<221> NAME/KEY: misc_feature
<222> LOCATION: (1)..(25)

<400> SEQUENCE: 19
agcaatgaga gatttgagac ttggt                                        25

<210> SEQ ID NO 20
<211> LENGTH: 19
<212> TYPE: DNA
<213> ORGANISM: Artificial Sequence
<220> FEATURE:
<223> OTHER INFORMATION: MAPT-R
<220> FEATURE:
<221> NAME/KEY: misc_feature
<222> LOCATION: (1)..(19)

<400> SEQUENCE: 20
ccttcgctgt cgctgtttc                                               19

<210> SEQ ID NO 21
<211> LENGTH: 19
<212> TYPE: DNA
<213> ORGANISM: Artificial Sequence
<220> FEATURE:
<223> OTHER INFORMATION: APH1 alpha-F
<220> FEATURE:
<221> NAME/KEY: misc_feature
<222> LOCATION: (1)..(19)

<400> SEQUENCE: 21
atgcacggct ccagtatgg                                               19
```

```
<210> SEQ ID NO 22
<211> LENGTH: 23
<212> TYPE: DNA
<213> ORGANISM: Artificial Sequence
<220> FEATURE:
<223> OTHER INFORMATION: APH1 alpha-R
<220> FEATURE:
<221> NAME/KEY: misc_feature
<222> LOCATION: (1)..(23)

<400> SEQUENCE: 22
gcaaaacgga acacttcctg tag                                              23

<210> SEQ ID NO 23
<211> LENGTH: 20
<212> TYPE: DNA
<213> ORGANISM: Artificial Sequence
<220> FEATURE:
<223> OTHER INFORMATION: GSK3 beta-F
<220> FEATURE:
<221> NAME/KEY: misc_feature
<222> LOCATION: (1)..(20)

<400> SEQUENCE: 23
cgggacccaa atgtcaaact                                                  20

<210> SEQ ID NO 24
<211> LENGTH: 20
<212> TYPE: DNA
<213> ORGANISM: Artificial Sequence
<220> FEATURE:
<223> OTHER INFORMATION: GSK3 beta-R
<220> FEATURE:
<221> NAME/KEY: misc_feature
<222> LOCATION: (1)..(20)

<400> SEQUENCE: 24
tccgagcatg tggagggata                                                  20

<210> SEQ ID NO 25
<211> LENGTH: 20
<212> TYPE: DNA
<213> ORGANISM: Artificial Sequence
<220> FEATURE:
<223> OTHER INFORMATION: GAPDH-F
<220> FEATURE:
<221> NAME/KEY: misc_feature
<222> LOCATION: (1)..(20)

<400> SEQUENCE: 25
tggtatcgtg gaaggactca                                                  20

<210> SEQ ID NO 26
<211> LENGTH: 20
<212> TYPE: DNA
<213> ORGANISM: Artificial Sequence
<220> FEATURE:
<223> OTHER INFORMATION: GAPDH-R
<220> FEATURE:
<221> NAME/KEY: misc_feature
<222> LOCATION: (1)..(20)

<400> SEQUENCE: 26
agtgggtgtc gctgttgaag                                                  20
```